(12) United States Patent
Lenzner

(10) Patent No.: US 10,571,442 B2
(45) Date of Patent: Feb. 25, 2020

(54) SAGNAC FOURIER SPECTROMETER (SAFOS)

(71) Applicant: Matthias Lenzner, Tucson, AZ (US)

(72) Inventor: Matthias Lenzner, Tucson, AZ (US)

( * ) Notice: Subject to any disclaimer, the term of this patent is extended or adjusted under 35 U.S.C. 154(b) by 0 days.

(21) Appl. No.: 15/341,104

(22) Filed: Nov. 2, 2016

(65) Prior Publication Data

US 2018/0120086 A1 May 3, 2018

(51) Int. Cl.
*G01N 33/00* (2006.01)
*G01J 3/453* (2006.01)
*G01J 3/00* (2006.01)
*G01J 3/45* (2006.01)
*G01J 3/18* (2006.01)
*G01J 3/12* (2006.01)

(52) U.S. Cl.
CPC ............ *G01N 33/0004* (2013.01); *G01J 3/00* (2013.01); *G01J 3/1804* (2013.01); *G01J 3/45* (2013.01); *G01J 3/4532* (2013.01); *G01J 3/4537* (2013.01); *G01J 2003/1208* (2013.01); *G01N 2033/0093* (2013.01)

(58) Field of Classification Search
CPC ............ G01B 9/02044; G01B 9/02015; G01B 2290/30; G01N 33/0004; G01N 21/35; G01N 21/33; G01N 21/3103; G01N 2033/0093
See application file for complete search history.

(56) References Cited

U.S. PATENT DOCUMENTS

| | | | |
|---|---|---|---|
| 2012/0086946 A1* | 4/2012 | Szarmes | G01J 3/1804 356/451 |
| 2012/0176622 A1* | 7/2012 | Kudenov | G01J 4/04 356/491 |

* cited by examiner

*Primary Examiner* — Hwa Andrew Lee

(57) ABSTRACT

A technique and device to determine the spectrum of electromagnetic radiation in a certain range of wavelengths comprising: splitting said radiation into more than one beam; let these beams counter-propagate in a Sagnac-type ring interferometer; and imprinting a wavelength-dependent angular tilt onto the wavefront of each beam by at least one dispersive element which preferably is a transmission grating or grism; and re-combining the multiple beams on a detector that exhibits spatial resolution and can therefore resolve the fringes formed by interference; and perform the mathematical operations to determine the spectrum of said radiation from the obtained interferogram, wherein the dispersive element is mounted on a stage providing linear and/or rotational movement.

10 Claims, 5 Drawing Sheets

SAGNAC FOURIER SPECTROMETER (SAFOS)

STATEMENT REGARDING FEDERALLY SPONSORED RESEARCH OR DEVELOPMENT

This invention was made with government support under Grant No. DE-SC0011446 awarded by the US Department of Energy. The government has certain rights in the invention.

CROSS-REFERENCE TO RELATED APPLICATION

Not applicable.

BACKGROUND OF THE INVENTION

The current invention relates to optical spectrometers, especially interferometric optical spectrometers. More particularly, the invention is a method and a device to measure the modified or unmodified spectrum of a light source with high resolution. Basically, there are two ways to get access to information about the spectral content of an electromagnetic wave in the optical range and the adjacent parts of the frequency spectrum, resulting in two kinds of optical spectrometer in existence. One option is to spectrally disperse the incoming radiation by a dispersive element like a prism or a grating. The so obtained frequency-dependent intensity pattern can then be imaged onto a detector with spatial resolution (e.g. a CCD or CMOS camera). If an appropriate relay imaging is involved, the complete spectrum within the bandwidth of the apparatus can be observed simultaneously. Usually, these spectrometers have an entrance slit; and the resolving power of the device increases with decreasing slit width. Consequently, the performance of such a device is a compromise between resolving power and detection threshold for low light intensity. A common embodiment of such a device is a Czerny-Turner spectrograph, comprising a rotatable plane grating between mirrors or lenses that image the entrance slit to the exit slit.

The second option is to use interference of the electric field of the radiation under test. For this, either a reference wave with known spectrum has to be used, or the radiation to be tested is split in two or more parts and an autocorrelation of the wave with itself is performed. The second way is usually preferred, since a reference source would severely limit the bandwidth or the operation range of the device. Commonly, the corresponding interferometric spectrometers are set up as Michelson or Mach-Zehnder interferometers. One of the two beams is temporally delayed with respect to the other and a variation of this delay yields a time-dependent interference pattern, which can be converted to a spectrum by way of Fourier transform. A common disadvantage of time-delay based Fourier-Transform Spectrometers (as opposed to dispersive spectrometers) is that all spectral components contribute noise to the measured signal. Fourier Transform Spectrometers and Fabry-Perot spectrometers are common embodiments of the interferometric kind, the latter one being an example for an input spectrum that is compared to a fixed reference spectrum (which is the transmission spectrum of the Fabry-Perot setup).

A further version of interferometric spectrometers is realized by generating Fizeau fringes, the spatial frequency of which contains information about the spectrum of the radiation under test. Here too, at least two beams are generated from the incoming light and are brought to interference under a defined angle. From the interferogram, the spectrum may again be obtained by way of a numerical Fourier transform. Differently from the Fourier transform spectrometers that use a temporal delay between the two interfering spectral functions, these spectrometers can collect the complete spectrum within the bandwidth of the device simultaneously without the need to move any parts.

A modern version of these Fizeau interferometers is the spatial heterodyne spectrometer (U.S. Pat. Nos. 5,059,027; 7,119,905; 7,330,267; 7,466,421; 7,773,229; and US Patent Applications with Publication Nos. 20050046858; 20090231592; 20100321688; 20130188181; 20140029004; 20150030503), where a reflective diffraction grating under Littrow angle causes the necessary wavefront tilt for close off-Littrow wavelengths. These spectrometers can be built compact and without moving parts, however, they generally require optical elements of high quality. They can realize a large resolving power due to the fact that fringe spectrum is heterodyned around the Littrow wavelength.

Another version, a modified Sagnac spectrometer (U.S. Pat. Nos. 7,433,044 and 8,736,844) is similar to the spatial heterodyne spectrometer in that it is built with at least two reflection gratings. The two interfering beams are the two counter-propagating beams of the Sagnac ring interferometer; the resulting fringe spectrum is heterodyned around the Littrow wavelength as well. In this device as well, high-quality optical components are necessary. If the wavelength range of this spectrometer needs to be changed on a continuous basis, high-precision rotational stages for the gratings are required, due to the sensitive dependence of the Littrow wavelength on the angle of incidence on the grating.

BRIEF SUMMARY OF THE INVENTION

The invention comprises a Sagnac interferometer used to determine the spectrum of an input beam by splitting the beam into at least two identical copies, spectrally dispersing each of these copies and recombining them on a spatially resolving detector. The interference pattern contains the spectrum, which can be retrieved by a Fourier transform. The dispersing elements are transmission gratings, in which the sum of diffraction angle and angle of incidence only weakly depends on the angle of incidence. In some embodiments, the disclosed system does not contain moving parts and the spectrum is recorded at one instant, making the device small, stable and fast. In some embodiments, the grating will be rotated to slightly change the center wavelength of the device, which yields the possibility to determine the peak wavelength of an emission line without the need to calibrate the device before.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

DETAILED DESCRIPTION OF THE INVENTION

Figure 1:
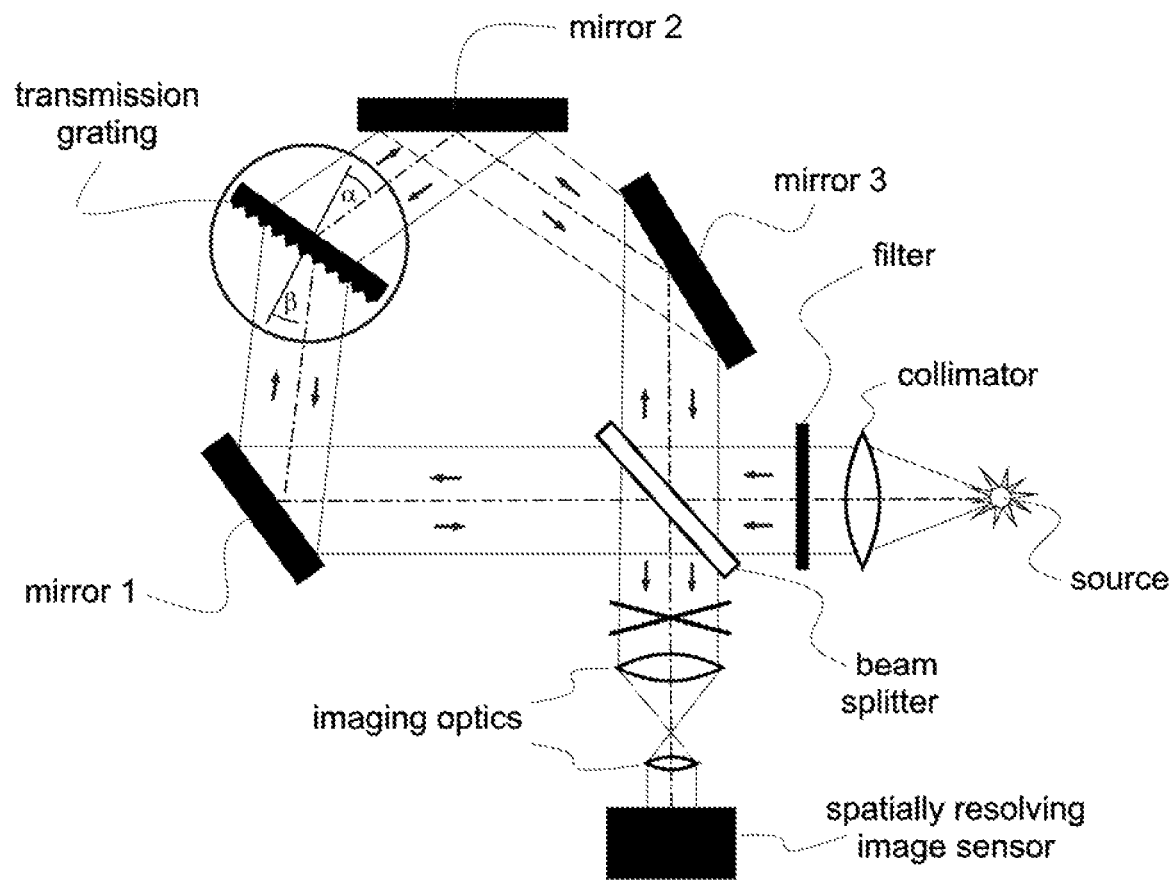
FIG. 1 shows one embodiment of a Sagnac Fourier Transform spectrometer, containing a single transmission grating as dispersive element.

The Sagnac Fourier Spectrometer (SAFOS) is basically a Sagnac interferometer (see FIG. 1, showing one embodiment of the disclosed system), in which at least one mirror is replaced by at least one transmission grating with grating constant g (=groove density, =number of lines per unit length), corresponding to a groove distance of d=1/g. The transmission grating is placed in a position that the Sagnac interferometer is realized for exactly one wavelength $\lambda_0$ given by the grating equation $$\sin \alpha + \sin \beta = g\lambda_0,$$

where $\alpha$ and are the angles which the beam forms with the grating normal, shown in FIG. 1. In the following, $\lambda_0$ is called the design wavelength. Light from the source under test, collimated by the collimator enters the SAFOS. It has to pass a filter, if large parts of the incident intensity are outside of the bandwidth of the apparatus, to avoid saturating the detector. The beam is split into two parts by the beam splitter and travels along a common path in different directions, deflected by mirror 1, mirror 2, and mirror 3, as indicated by the arrows in FIG. 1. It is dispersed by the transmission grating, recombined at the beam splitter and imaged by the imaging optics onto the spatially resolving image sensor. For the beam circulating counterclockwise in FIG. 1, a is the angle of incidence and $\beta$ is the diffraction angle for $\lambda_0$, while for the clockwise traveling beam, $\beta$ is the angle of incidence and $\alpha$ is the diffraction angle. Since the action of a transmission grating is reversible (sin $\alpha$+sin $\beta$=const.), both directions experience the same diffraction under the same angles at the design wavelength, where the setup works like a standard Sagnac interferometer. For a single wavelength (with zero bandwidth) and the device at rest, there is a homogeneous dark field in the output arm. For wavelengths off this design wavelength however, the wavefronts entering the output arm are slightly tilted under opposite angles for the two arms (shown by the two black lines in FIG. 1). Two tilted wave fronts of equal wavelength give rise to Fizeau fringes, which contain information about the spectrum of the source. An odd number of mirrors causes the two wave fronts in the output arm to be oppositely tilted. The interferogram will be finally recorded by a spatially resolving image sensor (e.g. a CCD camera), a Fourier transform of this interferogram yields the spectrum of the source. The common sign convention for transmission gratings is that angles on the same side of the grating normal have the same sign on both sides of the grating. Hence, in FIG. 1, both angles $\alpha$ and $\beta$ are positive. The wavelength $\lambda_0+\Delta\lambda$ is diffracted under the angle $\beta+\Delta\beta$, with $\Delta\beta=g\Delta\lambda/\cos\beta$. Consequently, the angular dispersion, $\Delta\beta/\Delta\lambda=g/\cos\beta$ increases with the angle $\beta$, obviously only limited by the clear aperture.

Figure 2:
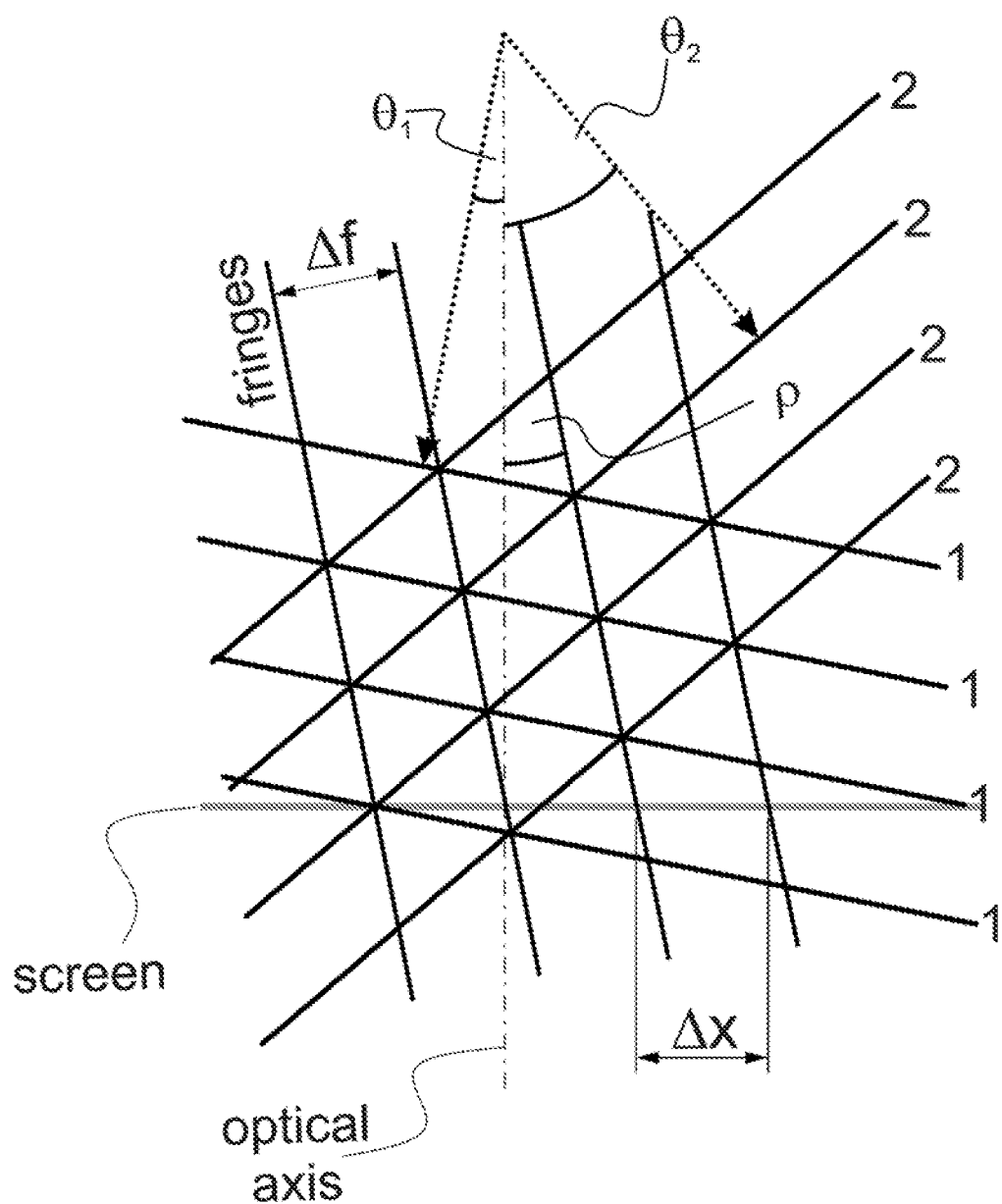
FIG. 2 shows two interfering wave fronts in the output arm of the disclosed device. The lines marked with '1' and '2' are the wave fronts of the two beams.

In contrast to the classical Fourier Transform Spectrometer, where the Fourier transform is performed from time to frequency, the Fourier transform is here performed from spatial frequency to wavelength. For this, we need to know the analytic dependence of the spatial frequency on the wavelength. In case of an asymmetric positioning of the grating ($\alpha\approx\beta$), the two wave fronts originating from the two directions exit the spectrometer under different angles, as shown in FIG. 2. This is due to the fact that the angular dispersion $\Delta\beta/\Delta\lambda$ depends on the diffraction angle.

The two angles are (see FIG. 2 for nominations):

$$\theta_1 = \frac{g\Delta\lambda}{\cos\beta} \text{ and } \theta_2 = \frac{g\Delta\lambda}{\cos\alpha}. \quad (1)$$

since $\alpha$ is the diffraction angle for one direction and $\beta$ for the other. The fringe spacing $\Delta f$ can be derived as in the symmetrical case by considering $(\theta_1+\theta_2)$ to be twice the tilt of one wavefront:

$$\Delta f = \frac{\lambda_0 + \Delta\lambda}{2\sin\frac{\theta_1+\theta_2}{2}}$$

In order to calculate the observed fringe spacing on a screen perpendicular to the optical axis, we need to know the angle between this axis and the fringes, which is:

$$\rho = \frac{\theta_1 - \theta_2}{2}$$

which yields the observed fringe spacing ($\Delta x=\Delta f/\cos\rho$):

$$\Delta x = \frac{\lambda_0 + \Delta\lambda}{2\sin\frac{\theta_1+\theta_2}{2}\cos\frac{\theta_1-\theta_2}{2}}$$

or, using a sum-to-product trigonometric identity:

$$\Delta x = \frac{\lambda_0 + \Delta\lambda}{\sin\theta_1 + \sin\theta_2}$$

or, using equation 1:

$$\Delta x = \frac{\lambda_0 + \Delta\lambda}{g\Delta\lambda\left(\frac{1}{\cos\alpha} + \frac{1}{\cos\beta}\right)}. \quad (2)$$

For the symmetric case ($\alpha=\beta$), we get $$\Delta x = \frac{(\lambda_0 + \Delta\lambda)\cos\beta}{2g\Delta\lambda}$$

From equation 2, we see that the factor quantifying the mapping of spatial fringe frequency ($1/\Delta x$) to wavelength ($\Delta\lambda$) depends on the angular position of the grating, i.e. on the diffraction angle $\beta$. Expressing $\alpha$ in equation 2 by the grating equation, we get:

$$\frac{1/\Delta x}{\Delta \lambda} = \frac{1}{\Delta x \Delta \lambda} \qquad (3)$$
$$= \frac{g}{\lambda_0}\left(\frac{1}{\cos\alpha} + \frac{1}{\cos(\arcsin(\lambda_0 g - \sin\alpha))}\right)$$

while assuming that $\Delta\lambda \ll \lambda_0$.

There are two ways to maximize the throughput of the system (i) operating the grating in first order and choose groove density and wavelength range such that only one first order is above the horizon of the grating or (ii) choose a blazed transmission grating for a higher order.

Due to the tilt of k-vector into and out of the grating, the energy front experiences a tilt that is different from the tilt of the wavefront [M. Lenzner and J. C. Diels, Optics Express, volume 24 (2016) page 1829]. The tilt angle of the energy front $\delta$ in the output arm can be calculated as tan $\delta = \lambda_0 \, d\epsilon/d\lambda$ [Z. Bor and B. Rácz, Optics Communications, volume 54 (1985) page 165]. $d\epsilon/d\lambda$ is the angular dispersion, which in our case is $\Delta\beta/\Delta\lambda$. From the angular dispersion listed above, we get:

$$\tan\delta = \frac{\lambda_0 g}{\cos\beta} = \frac{\sin\alpha + \sin\beta}{\cos\beta} \qquad (4)$$

In one embodiment of the disclosed device, the grating can be rotated. As evident from FIG. 1, the angle $\gamma = \pi - (\alpha+\beta)$ is fixed, defining the optical axis of the Sagnac ring. When the grating is rotated, the angle of incidence $\alpha$ changes. Since $\alpha+\beta$=const. does in general not imply that $\sin\alpha + \sin\beta$=const., the grating equation is fulfilled for a different wavelength after the rotation. Consequently, the wavelength propagating along the optical axis is not determined by:

$$\lambda = \frac{1}{g}[\sin(\alpha) + \sin(\alpha + \gamma)] \qquad (5)$$

This equation shows, for a given initial spectrometer configuration (fixed $\gamma$ and g), how the center wavelength changes when the grating is rotated by an angle $\delta$. Again, if radiation at this wavelength is incident, no Fizeau fringes are observed, just a bright field. Only components that are off this center wavelength can be measured.

Figure 3:
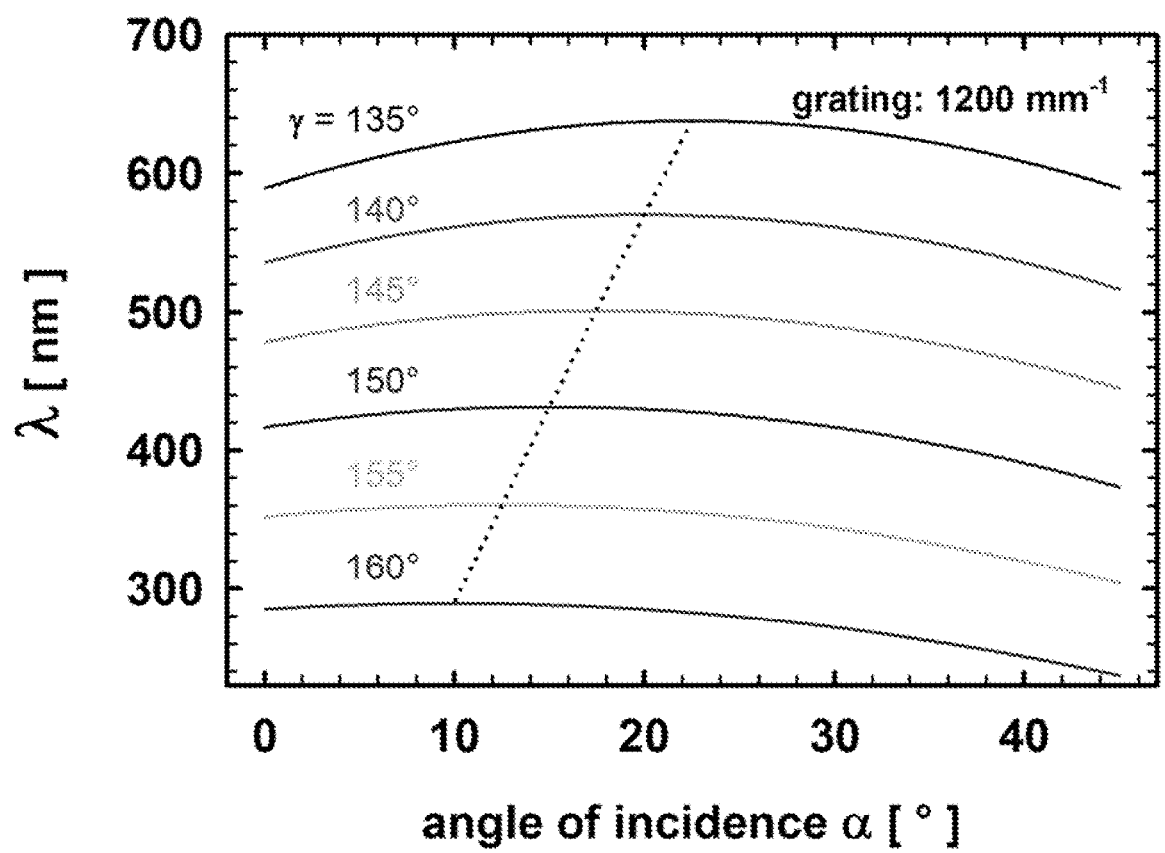
FIG. 3 is a plot of the wavelength propagating on the optical axis, when the transmission grating is rotated. The dotted line connects the maxima of the curves, where $\alpha=\beta$.

As an example, FIG. 3 shows this deviation for a spectrometer configured with g=1200 mm$^{-1}$ and several design angles $\gamma$. By differentiating equation 5 with respect to $\gamma$, one finds that the maximum of the curve is at $\alpha=\beta=(\pi-\gamma)/2$. Consequently, the curve has a maximum at $\lambda_D$=2 cos($\gamma/2$)/g. Obviously, $\alpha=\beta$ determines the largest center wavelength for a given design, this corresponds to the design wavelength of the spectrometer. Note that the curve is not symmetric and that the curvatures are different for different design angles.

The fact that the wavelength range under investigation must not overlap with the wavelength propagating along the optical axis dictates the operational conditions of the SAFOS. One embodiment of the disclosed device operates in the same way as the Spatial Heterodyne Spectrometer [J.

Figure 4:
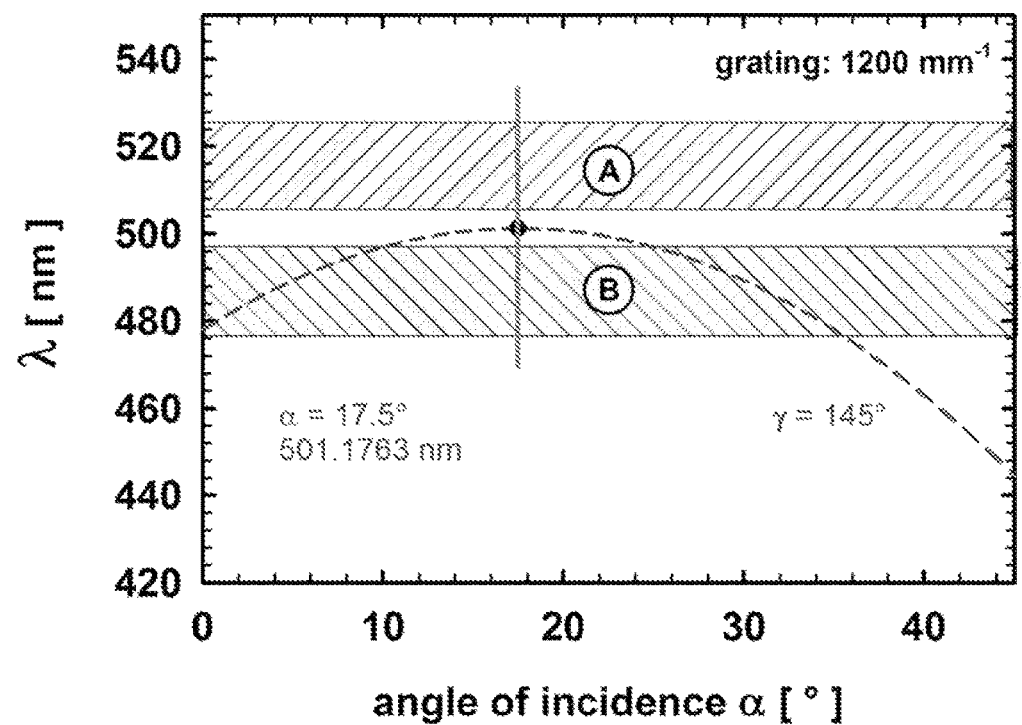
FIG. 4 plots the characteristic range for an embodiment of the disclosed device, operating with a fixed grating. The vertical line shows the range of operation, A and B denominate the usable bandwidth. The tuning curve if the grating would be rotated is shown for orientation, the vertical line could be placed on any position on this curve, with the corresponding shift of ranges A and B.

Harlander, R. J. Reynolds, F. L. Roesler, The Astrophysical Journal, vol. 396 (1992) page 730]: the grating positioned under a fixed angle, covering a wavelength range to either side of the design wavelength. The distance between design wavelength and the limit of the usable wavelength ranges is dictated by the mathematical processing. If it is too small, the wavelength to be measured overlaps with the zero-frequency spike of the Fourier transform and cannot be sensibly extracted anymore. This configuration, for $\alpha=\beta$, is shown in FIG. 4, the vertical line denominating the operation range of the spectrometer. For any fixed angle $\beta$, the standard Fourier transform, including the scaling parameter $$\frac{1}{\Delta x \Delta \lambda} = \frac{2g}{\lambda_0 \cos\beta}$$

can be used. Consequently, we have a spectrometer without moving parts; however, there would still be the ambiguity that spectra mirrored on the design wavelength would yield the same interferogram.

Figure 5:
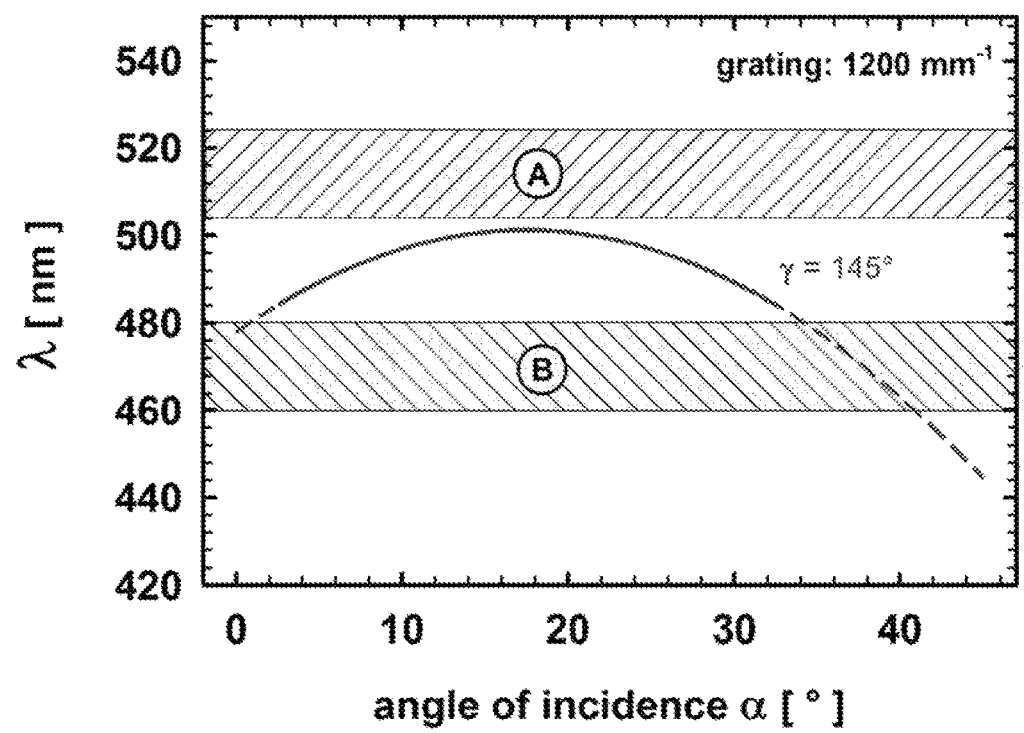
FIG. 5 plots the characteristic range for an embodiment of the disclosed device operating with adjustable grating angle. The ambiguity, on which side of the design wavelength the measured wavelength is located, can be resolved by moving the grating. The dashed line shows the extension of the tuning cure beyond the usable range.

In a further embodiment of the disclosed device, using the very weak dependence of the center wavelength on the grating angle as shown in FIG. 3, one can use two ranges as well, as shown in FIG. 5. The range B however, has to be placed further away from the design wavelength. This configuration opens the possibility to resolve the ambiguity concerning the sign of $\Delta\lambda$. By scanning the angle of incidence, the spectrum will move one way or the other, the direction of which tells the sign.

As can be seen from FIG. 3, all curves $\lambda(\alpha)$, generated by rotation of the grating for an angle $\alpha$ have different curvature for different design angles $\gamma$. Consequently, if a certain wavelength is sent into the spectrometer, this wavelength can be measured without any prior knowledge about the spectrometer setup by rotating the grating and measuring the curvature $d^2\lambda/d\alpha^2$.

An example for a mathematical sequence that serves this purpose is:
1. Coarsely set the design angle of the spectrometer to a value that corresponds to a wavelength larger than the peak wavelength of the incident radiation
2. Record interferograms in dependence on $\Delta\alpha$, which is the change of the grating angle referring to an arbitrarily chosen value.
3. A value $\lambda_D$ (the design wavelength) is required to perform the Fourier Transform. For the first run, an estimated value can be used.
4. Fit the equation $$\lambda = \lambda_0 + \frac{1}{g}[\sin(\alpha + \Delta\alpha) + \sin(\alpha + \Delta\alpha + \gamma)]$$

with free parameters $\alpha$, $\gamma$, and $\lambda_0$ to the experimental values
5. The maximum of the curve occurs at $\lambda_{max}(\alpha_{max})$ with $\alpha_{max}=\frac{1}{2}(\pi-\gamma)$, this is an additional test of the quality of the fit or could serve as an additional constraint.
6. If necessary, set $\lambda_D=\lambda_{max}+\lambda_0$ and repeat the procedure starting at point 3.

The invention claimed is:
1. A Sagnac Fourier spectrometer for determining the spectrum of incident light comprising:
   means to collect the incoming light such that it propagates as a collimated beam;

means to limit the wavelength band of the incoming light;

means to split the incident light into a first beam and a second beam such that the two have equal or nearly equal polarization and subsequently combine first beam and second beam such that the first beam and the second beam propagate on the same optical path in opposite directions and after combination overlap spatially coherently to form an interference pattern;

means to impose a spatial or angular dispersion onto the first beam and onto the second beam by one or more transmission gratings;

wherein on the optical path the two counter-propagating beams are angular or spatially dispersed by said dispersive devices such that radiation of one wavelength propagates along said optical path in both directions;

means to detect and record the output beam as a spatially resolved image in one or two dimensions, in the following called the image sensor;

means to receive the spatially resolved intensity information from the image sensor and computationally process it into a spectrum.

2. The apparatus of claim 1, wherein said filter comprises a band pass filter, a short pass filter, a long pass filter, and combinations thereof.

3. The apparatus of claim 1, wherein said transmission gratings are mounted on a translation and/or rotation stage, causing the apparatus to work in a variable wavelength range.

4. The apparatus of claim 1, wherein said transmission gratings are mounted in a fixed position, causing the apparatus to work in a fixed wavelength range.

5. The apparatus of claim 1, wherein the spectrum of incident light occupies the infrared part of the electromagnetic spectrum and the combination of said transmission gratings and said image sensor are designed to process the infrared part of the spectrum.

6. The apparatus of claim 1, wherein the spectrum of incident light occupies the visible part of the electromagnetic spectrum and the combination of said transmission gratings and said image sensor are designed to process the visible part of the spectrum.

7. The apparatus of claim 1, wherein the spectrum of incident light occupies the ultraviolet part of the electromagnetic spectrum and the combination of said transmission gratings and said image sensor are designed to process the ultraviolet part of the spectrum.

8. The apparatus of claim 1, wherein the combination of said transmission gratings and said image sensor is designed to determine the isotopic shift of emission lines in atoms and molecules.

9. The apparatus of claim 1, wherein the combination of said transmission gratings and said image sensor is designed to measure the spectra of Uranium and Plutonium.

10. The apparatus of claim 1, wherein the combination of said transmission gratings and said image sensor is designed to measure the spectra of aerosols.

* * * * *